(12) United States Patent
Romero

(10) Patent No.: US 9,060,509 B2
(45) Date of Patent: *Jun. 23, 2015

(54) THERMAL PACKAGING SYSTEM FOR BLOOD AND ORGANS

(71) Applicant: TCP Reliable, Inc., Edison, NJ (US)

(72) Inventor: Benjamin Romero, San Mateo, CA (US)

(73) Assignee: TCP Reliable, Inc., Edison, NJ (US)

( * ) Notice: Subject to any disclaimer, the term of this patent is extended or adjusted under 35 U.S.C. 154(b) by 253 days.

This patent is subject to a terminal disclaimer.

(21) Appl. No.: 13/707,564

(22) Filed: Dec. 6, 2012

(65) Prior Publication Data
US 2014/0157799 A1 Jun. 12, 2014

Related U.S. Application Data

(63) Continuation of application No. 13/401,321, filed on Feb. 21, 2012, now Pat. No. 8,316,662, which is a continuation of application No. PCT/US2004/025314, filed on Aug. 4, 2004, which is a continuation of application No. 10/637,824, filed on Aug. 7, 2003, now Pat. No. 7,294,374, application No. 13/707,564, which is a continuation of application No. 13/672,854, filed on Nov. 9, 2012, now Pat. No. 8,505,314.

(51) Int. Cl.
| | |
|---|---|
| *F25D 3/10* | (2006.01) |
| *A01N 1/02* | (2006.01) |
| *F25D 3/08* | (2006.01) |
| *A61J 1/05* | (2006.01) |
| *B65D 81/38* | (2006.01) |
| *A61J 1/16* | (2006.01) |

(52) U.S. Cl.
CPC ............ *A01N 1/0273* (2013.01); *F25D 3/08* (2013.01); *F25D 2303/08221* (2013.01); *F25D 2303/0844* (2013.01); *F25D 2303/0845* (2013.01); *F25D 2303/085* (2013.01); *F25D 2331/804* (2013.01); *A61J 1/05* (2013.01); *A61J 1/165* (2013.01); *A61J 2200/44* (2013.01); *B65D 81/3834* (2013.01)

(58) Field of Classification Search
CPC ... F25D 3/08; F25D 3/10; F25D 2303/08221; F25D 2303/0844; F25D 2303/0845; F25D 2303/085; F25D 2331/804; A01N 1/0273; B65D 81/3834; A61J 1/05; A61J 1/165; A61J 2200/44
USPC .......................................... 62/60, 457.2, 529
See application file for complete search history.

(56) References Cited

U.S. PATENT DOCUMENTS

| | | | |
|---|---|---|---|
| 4,931,333 A | 6/1990 | Henry | |
| 5,087,508 A | 2/1992 | Beck et al. | |
| 5,647,226 A * | 7/1997 | Scaringe et al. | 62/457.2 |
| 6,044,650 A | 4/2000 | Cook et al. | |
| 8,316,662 B2 * | 11/2012 | Romero | 62/430 |
| 2005/0031809 A1* | 2/2005 | Romero | 428/34.1 |
| 2008/0057574 A1* | 3/2008 | Romero | 435/307.1 |
| 2011/0020429 A1* | 1/2011 | Lauten et al. | 424/450 |

* cited by examiner

*Primary Examiner* — Michael C Miggins
(74) *Attorney, Agent, or Firm* — Eric P. Mirabel

(57) ABSTRACT

The present invention is an apparatus, method and system to thermally package an item having at least one container (100) substantially filled with an alcohol, wherein said alcohol undergoes a phase change.

20 Claims, 6 Drawing Sheets

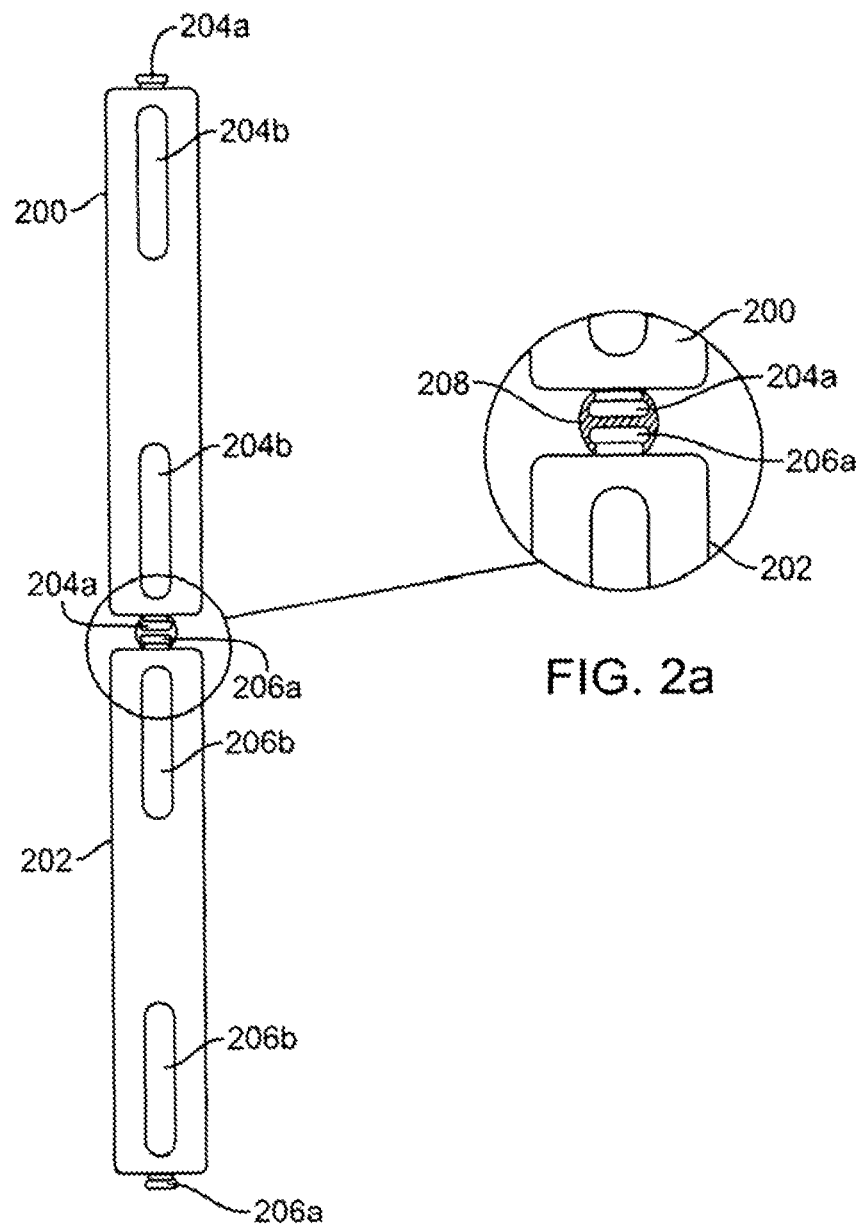

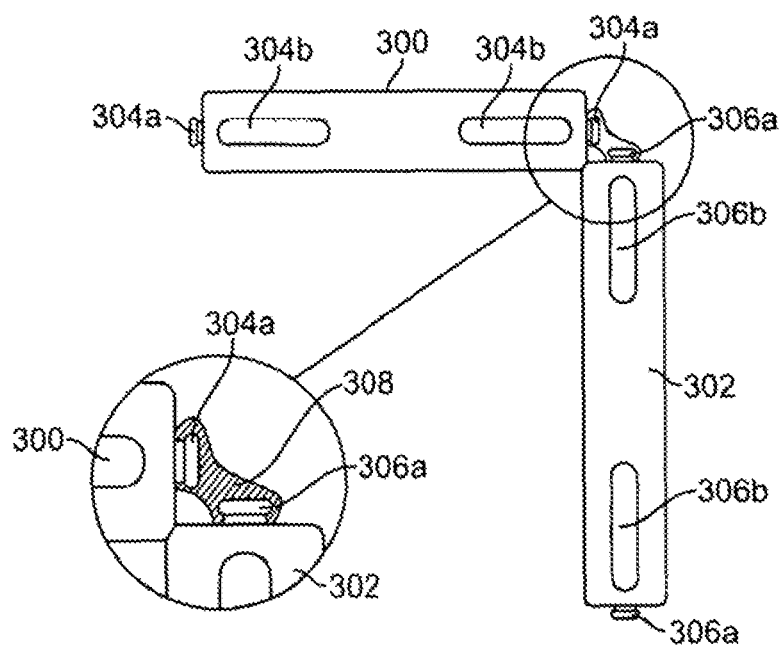

THERMAL PACKAGING SYSTEM FOR BLOOD AND ORGANS

RELATED APPLICATIONS

This application is a continuation of and claims priority to Ser. No. 13/672,854, filed Nov. 9, 2012, which is a continuation of U.S. application Ser. No. 13/401,321, filed Feb. 21, 2012 (U.S. Pat. No. 8,316,662), which is a continuation of International Application No. PCT/US04/25314, filed Aug. 4, 2004, which is a continuation of U.S. application Ser. No. 10/637,824, filed Aug. 7, 2003 (U.S. Pat. No. 7,294,374).

FIELD OF THE INVENTION

The present invention relates to packaging systems. More particularly, the present invention relates to thermal packaging systems for products that must be packaged in a temperature-controlled environment.

BACKGROUND OF THE INVENTION

The use of refrigerants to keep items cool is widespread, both for transportation of heat sensitive or heat dameageable products and for long term storage of the products. Refrigerators and refrigerated transport systems can be used for storage and transportation of large scale products, but may not be available for small scale products such as short haul delivery systems, airline transportation, and home and recreational cooling of foods, beverages and the like.

The use of ice, dry ice, or blue ice to keep products at a cool temperature has been used extensively for many years. For example, the general public widely uses insulated containers packed with ice to maintain foodstuffs and beverages cool when camping, travelling or on picnics and the like. Ice is also used commercially to pack foodstuffs, flowers, plants and the like for transportation and storage until sold or until placed in a refrigerator. Ice is also used in the medical field to reduce trauma, swelling and pain from injuries of all kinds, and to transport and store blood, tissue, organs, pharmaceuticals and the like. The use of ice, dry ice, or blue ice as a coolant material serves as a preservative and inhibits the growth of harmful microorganisms.

The major drawback to the use of ice as a coolant material is that it melts and is no longer an effective packaging material. The melted ice is easily contaminated by microorganisms which, since it will be in intimate contact with the products it is protecting, is also liable to contaminate the products. The items may also be damaged by getting wet. The melted ice may also allow the products to move or slosh around in the container, risking damage by impact with the walls of the container. Moreover, the container itself must also be waterproof or the water and the products will break out of the container.

Dry ice also has some disadvantages. It is converted into $CO_2$ with time and thus the gas must be dissipated and the product will not be packed against movement in its container or be kept cool. Both water and dry ice can be used only once, adding to the expense of thermal storage.

Blue ice may be used repeatedly by refreezing the contents of the bag or block. However, blue ice is brick hard when frozen into a solid block and becomes soft and pliable as the material melts within the bag.

Ice, dry ice, and blue ice may be used to keep items or products cool, however, a user has no control over the temperature of the container or the products. Currently, there is no way to maintain the temperature of products unless a refrigerator or refrigerated transport system is used. Moreover, when used, the ice, dry ice, and blue ice move around within the package that may create temperature variances within the packaging. Thus, some parts of the products may be cool while other parts are warm.

Thus, there is a need for an apparatus and method that allows a use to maintain a constant known temperature over an extended period of time in a container without the use of refrigerators or refrigerated transport systems at an economical cost. Moreover, there is a need for a reusable apparatus that allows a user to maintain a constant known temperature in a container with little to no temperature variances within the packaging.

BRIEF DESCRIPTION OF THE INVENTION

The present invention is an apparatus, method and system to thermally package an item having at least ne container substantially filled with an alcohol, wherein said alcohol undergoes a phase change.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

In the drawings:

FIGS. 2 and 2a illustrate top views of an example to releasably lock thermal packs together in accordance with an embodiment of the present invention.

FIGS. 3 and 3a illustrate top views of an example to releasably lock thermal packs together at a corner in accordance with an embodiment of the present invention.

DETAILED DESCRIPTION

Figure 1A:
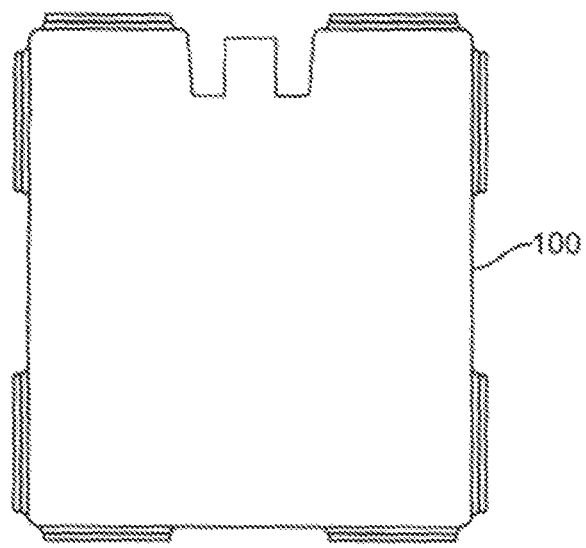
FIGS. 1A, 1B, and 1C illustrate examples in which the phase change material may be packaged.

Embodiments of the present invention are described herein in the context of a thermal packaging system. Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

The present invention is an apparatus, method, and system that allows a user to maintain a constant known temperature over an extended period of time in a container with little to no temperature variances within the container. The present invention utilizes the phase change properties of various phase change materials, specifically of alcohols. Different mixtures, cuts and blends of alcohols may be used. In an embodiment of the present invention, the alcohols used have a purity of between 90%-100%. However, those of ordinary skill in the art will now realize that any linear or branched alcohol of varying purity may be used in the present invention. Phase change is the property of a material by which when turning from solid to liquid (or vice versa), energy is absorbed or released without a change in temperature of the material. The phase change material, used in the present invention may change from solid to liquid (and vice versa) at different temperatures. By way of example, blood platelets and biological tissues are chemically unstable in high temperatures and must be maintained between 20° C. and 24° C. I-Dodecanol, a linear alcohol, has phase change at about 20° C.-24° C., a ideal temperature to maintain the blood platelets or tissue in a container. The present invention may be used to control the temperature of such products during transport by confining the temperature of the product within a predetermined range. The use of linear or branched alcohols allow for a relatively constant temperatures as it undergoes a phase change. This permits light weight packaging with the maintenance of temperatures in narrow, pre-selected ranges over extended periods of time.

The phase change material used in the present invention may be an alcohol such as a linear alcohol or branched alcohol. By way of example only, and not intended to be limiting, examples of linear alcohols that may be used in the present invention are 1-Dodecanol and I-Decanol. In an embodiment of the present invention, the alcohol may have between about 6 to 20 carbon atoms.

I-Dodecanol is also known as Dodecyl alcohol, lauryl alcohol, Duodecyl alcohol, and Lauric alcohol. I-Dodecanol is a saturated fatty alcohol having a chemical formula of:

$CH_3CH_2CH_2CH_2CH_2CH_2CH_2CH_2CH_2CH_2CH_2CH_2OH$

I-Dodecanol is a colorless solid and liquid and is insoluble in water. Its phase change property at about 20° C.-24° C. allows for a user to maintain the temperature of products at a known temperature of around 20° C.-24° C. I-Dodecanol has a low toxicity, is non-hazardous, and is relatively inexpensive.

1-Dodecanol is currently used primarily as a chemical intermediate for the production of n-Dodecyl sulfate salts, and in the manufacture of n-Dodecyl ethoxylates. It is also used in synthetic detergents, lube additives, pharmaceuticals, as a flavoring agent in foods, cosmetics, rubber, textiles, lotions and creams, and perfumes. By way of example, I-Dodecanol has been found in fillers and insulating materials for the building industry, part of foaming and surface-active agents for cleaning purposes, and in metal refining and processing. It has also been found in ice cream, candy, baked goods, chewing gum, and syrups. However, until now, I-Dodecanol has never been used or known as a phase change packaging material to package temper re sensitive products.

I-Decanol is also known as capric alcohol, royaltac, decanol, n-decanol, decyl alcohol, caprinic alcohol, and n-decyl alcohol. I-Decanol is a saturated fatty alcohol haying a chemical formula of:

$CH_3CH_2CH_2CH_2CH_2CH_2CH_2CH_2CH_2CH_2OH$

I-Decanol has a phase change at about 2° C.-8° C. that allows for a user to maintain the temperature of products at a known temperature of around 2° C.-8° C. Thus, I-Decanol may be used to protect products between 2° C. to 8° C., which is the required temperature for many pharmaceutical products.

Similar to I-Dodecanol, I-Decanol is currently used in household laundry detergents, shampoos, cosmetics, and industrial processes, lubricant additives, and germicidal and fungicidal products, and fabric softeners, just to name a few uses.

Figure 1B:
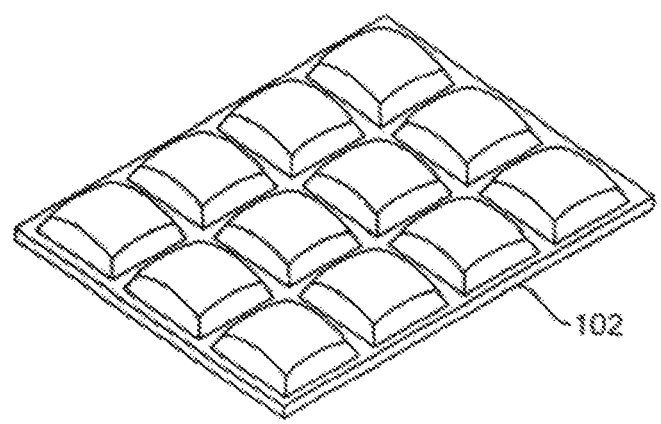
Figure 1C:
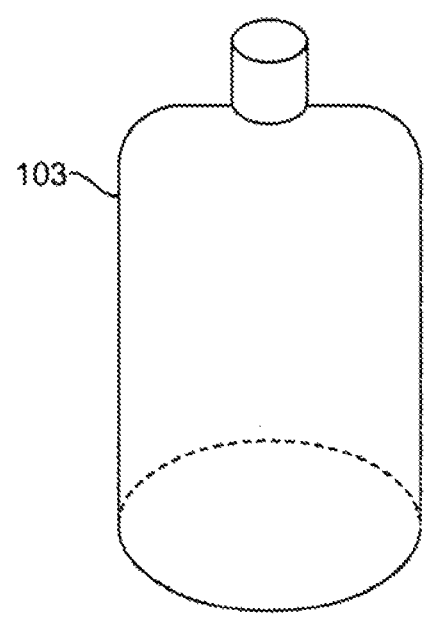

FIGS. 1A, 1B, and 1C illustrate the various containers in which the phase change material may be packaged. The phase change material may be substantially contained in various containers or packs such as bags, shaped containers (a square container is illustrated herein) 100, gel blankets 102, bottles 103, sponges and other porous materials, recirculating systems, single and multi-wall plastic assemblies, or other similar containers. The phase change materials may be placed within the containers through an opening in the containers. The containers may be made of various materials such as high-density polyethylene, low-density polyethylene, or any other similar materials. Those of ordinary skin in the art will now realize that any materials that are chemically compatible and stable with the phase change material may be used.

The container and the phase change material may be reusable, thus allowing for a low cost packaging solution. Moreover, the thermal packaging system is in weight and volume and allows for an equal distribution of temperature within an outer container used to house the phase change material and products.

Releasable locking means on the container may protect the products from temperature variance within the packaging and may also protect the products against damage from shock and vibration during transit. FIGS. 2, 2a, 3, and 3a illustrate top views of an example to releasable lock the thermal packs together in accordance with an embodiment of the present invention. FIGS. 2 and 2a illustrate an example to releasably lock two containers together in a side-by-side configuration. Containers 200 and 202 may have a connector 204a, 204b, 206a, 206b on each side of containers 200 and 202.

Connectors 204a and 206a may be connected using a releasable lock 208 whereby connectors 204a and 206a may slidably fit into grooves in releasable lock 208. Releasable lock 208 may have a bottom (not shown) to prevent connectors 204a and 206a from sliding out. The releasable locking means helps to thermally protect the products from temperature variances by preventing the containers from sliding, changing positions or shifting around each other. This further aid in the ability for greater validation of the products for transit.

FIGS. 3 and 3a illustrate an example to releasably lock two containers together at a corner. Containers 300 and 302 may have connectors 304a, 304b, 306a, 306b on each side of containers 300 and 302. Similar to FIG. 2a, a releasable lock 308 may be used to connect connectors 304a and 306a whereby connectors 304a and 306a may slidably fit into the grooves in releasable lock 308. Releasable lock 308 may have a bottom (not shown) to prevent connectors 304a and 306a from sliding out. Releasable lock 308 is V shape that allows for containers 300 and 302 to be positioned at an angle relative to each other.

Those of ordinary skill in the art will no realize that there may be other is to releasably lock the containers together and prevent them from easily coming apart such as the use of Velcro, snaps, and other similar releasable locking means. Moreover, the releasable locks may be positioned on any surface of a container to prevent possible movement of the containers in any direction. For example, the releasable locks may be positioned on a front and back surface of the container such that the containers may be stacked upon each other. Furthermore, FIGS. 2 and 3 illustrate two releasable locks on the containers. However, that is not intended to be limiting since any number of releasable locks may be placed on the containers as is necessary such as one or three.

Figure 4:
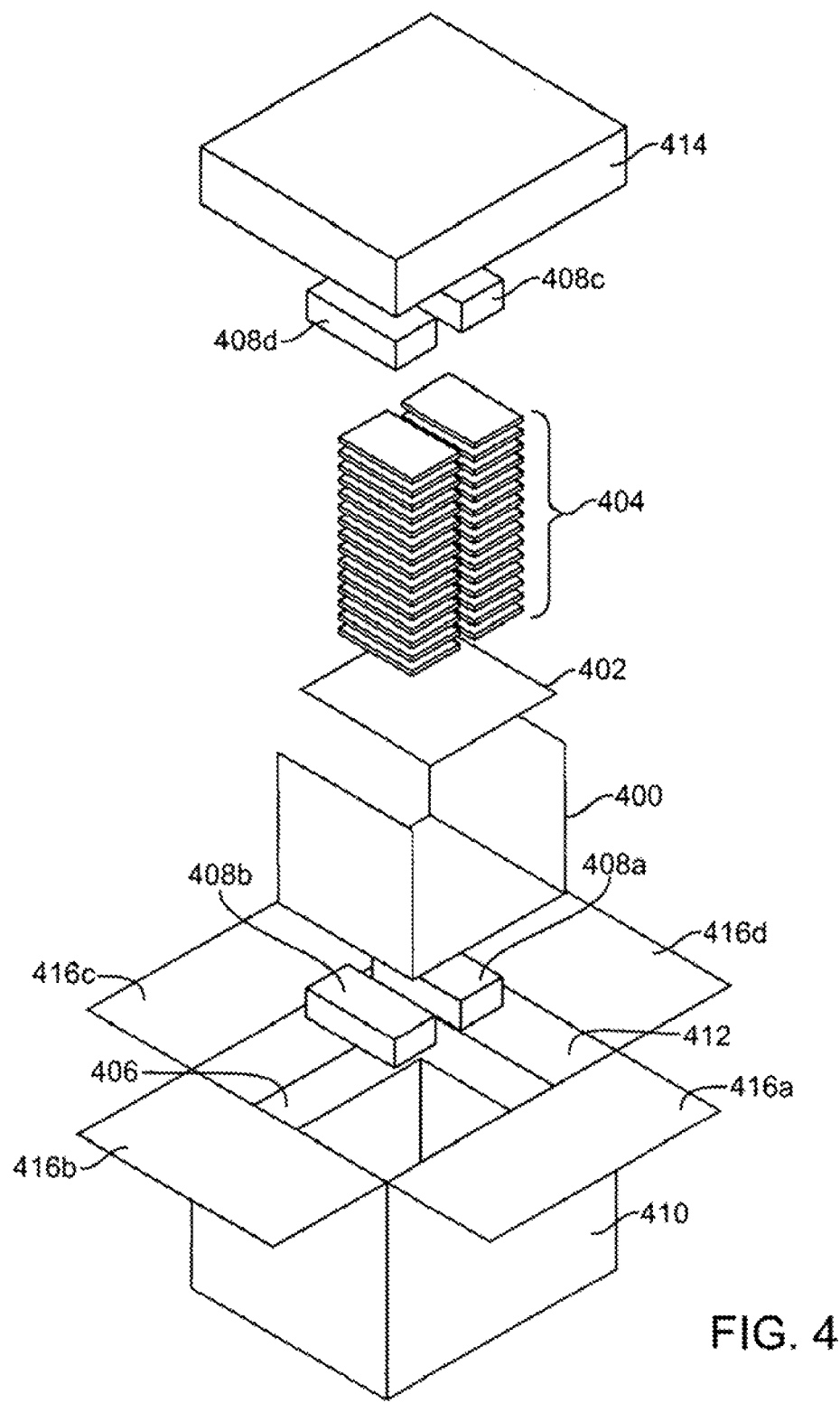
FIG. 4 illustrates a system in accordance with an embodiment of the present invention.

The present invention provides for a system of using the phase change material as illustrated in FIG. 4. The items 404 to be thermally protected are packaged in a first container 400. By way of example and not intended to be limiting, the items 404 may be blood platelet bags. The first container 400 may be a plastic bag, or the like. An absorbing pad 402 may be placed below the items 404 to provide for added protection from wetness or shock. The first container 400 may or may not be sealed.

A second container 406 may be used to house the first container 400. Thermal packs 408a, 408b, 408c, 408d may be positioned within the second container 406 above and below the first container 400. The thermal packs may be substantially filled with 1-Dodecanol to keep the items 404 at a constant temperature of about 20° C.-24° C. Although the thermal packs are illustrated as brick shaped containers, those of ordinary skill in the art will now realize that other shapes may be used. Moreover, as described above, the thermal packs may be connected together in the manner described above to protect the items 404 from temperature variances within the container and may protect the product from damage. A second container lid 414 may be used to seal the second container 406.

Once positioned within the second container 406, the second container 406 is then positioned in a third container 410. The third container 410 may comprise of padding or insulating material 412 around the inner periphery of the container 410. However, it will be appreciated that thermal packs may be used in addition to or instead of padding or insulating material 412. The insulating shipping materials made be made of materials such as expanded polystyrene, urethane, vacuum panels, or other similar insulation materials. The third container 410 may also have a third container lid 416a, 416b, 416c, 416d to seal the third container 410.

The first, second, and third containers, as well as the thermal packs may all be reusable thereby adding to the efficiency and low cost of the present invention.

Figure 5:
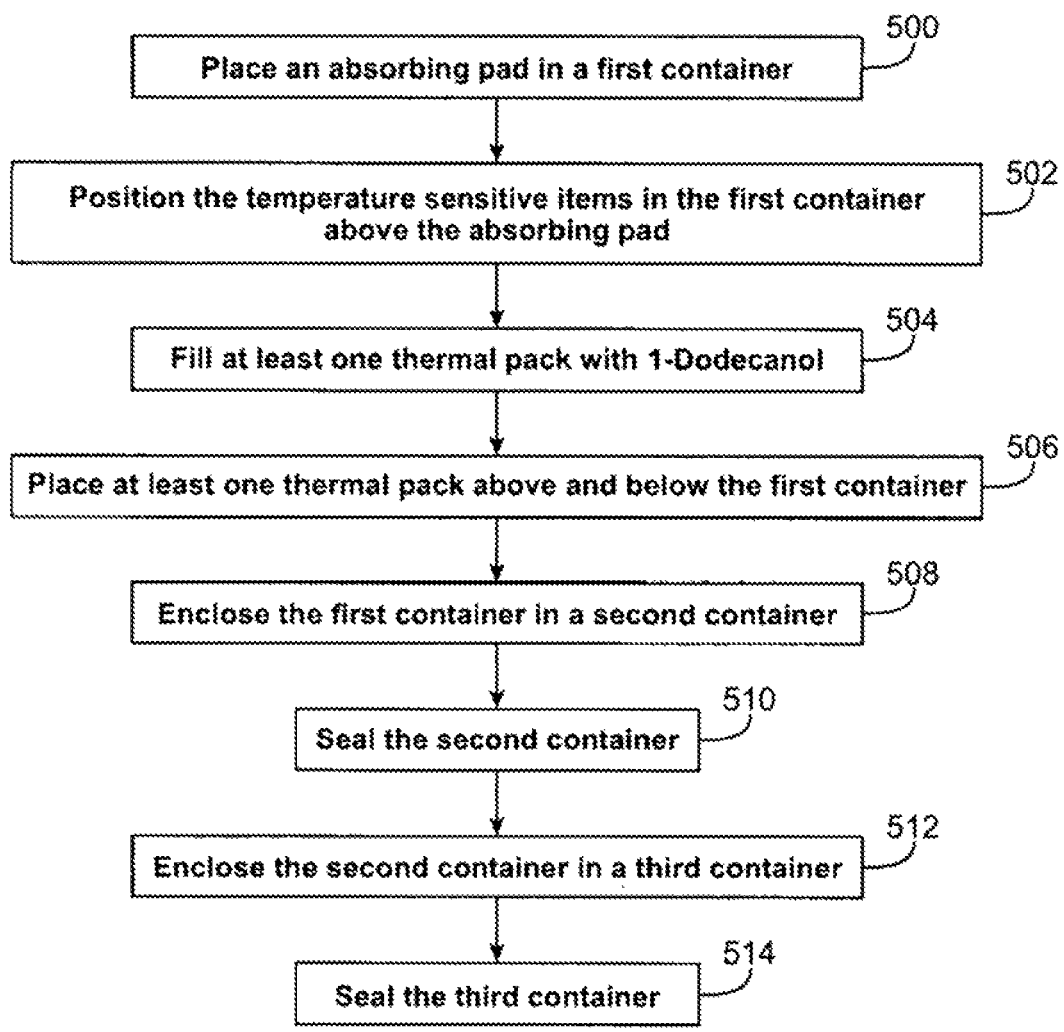
FIG. 5 is a block diagram of a method in accordance with an embodiment of the present invention.

FIG. 5 is a block diagram of a method in accordance with an embodiment of the present invention. An absorbing pad may be placed in a first container at 500 to provide added protection from wetness or shock. The items may then be positioned in the first container above the absorbing pad at 502. However an absorbing pad does not need to be used and the first container may or may not be sealed.

At least one thermal pack may be filled with an alcohol at 504. The thermal packs may then be positioned above and below the first container at 506. The first container may then be enclosed in a second container at 508 and the second container may be sealed at 510 to maintain the temperature of the items at around 20° C.-24° C. The second container may then be enclosed in a third container at 512. The third container may contain a padding or insulating material around the inner periphery of the container.

However, it will be appreciated that thermal packs may be used in addition to or instead of padding or insulating material. The third container may then be sealed at 514.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims.

What is claimed is:

1. A process for maintaining blood or organs during shipment at about 2° C. to 8° C., comprising:
substantially filling at least one first container with a eutectic solution consisting essentially of substantially pure 1-decanol;
placing said first container either adjacent to or inside of a second container containing the blood or organs; and
placing the first and second containers inside a third container.

2. The process of claim 1 wherein several first containers are placed adjacent to or inside of the second container.

3. The process of claim 1 wherein the second container is a plastic bag which may or may not be sealed.

4. The process of claim 1 wherein the third container has insulating properties.

5. The process of claim 1 wherein said first, second, third, and fourth containers are reusable.

6. The process of claim 1 further including placing at least one absorbing pad between said second container and said blood or organs.

7. The process of claim 1 wherein the first container is a blanket having several cells which are substantially filled with the eutectic solution.

8. The process of claim 1 wherein said eutectic solution is said eutectic solution is about 98% 1-decanol.

9. The process of claim 8 wherein said eutectic solution is about 98.7% 1-decanol, about 0.5% 1-octanol, and about 0.09% moisture.

10. The process of claim 1 further including a fourth container surrounding the third container.

11. The process of claim 10 wherein the fourth container is sealed.

12. The process of claim 10 wherein said fourth container further comprises an insulating material surrounding an inner periphery of said fourth container.

13. The process of claim 10 wherein said fourth container further comprises at least one first container surrounding an inner periphery of said fourth container.

14. The process of claim 10 wherein the fourth container is sealed with a lid.

15. The process of claim 1 further including mating each of said at least one first containers.

16. The process of claim 15 wherein the first containers are thermal packs which are releasably mated.

17. The process of claim 16 wherein the releasable mating of the thermal packs comprises a releasable lock.

18. The process of claim 16 wherein the releasable mating of the thermal packs comprises a flexible lock.

19. The process of claim 1 wherein the third container is sealed with a lid.

20. The process of claim 19 wherein said lid is positioned on top of the third container.

* * * * *